(12) United States Patent
Fuchs et al.

(10) Patent No.: US 12,109,390 B2
(45) Date of Patent: Oct. 8, 2024

(54) INFUSION SYSTEM HAVING AN INFUSION PUMP AND HAVING A PUMP MODULE THAT CAN BE COUPLED THERETO

(71) Applicant: B. Braun Melsungen AG, Melsungen (DE)

(72) Inventors: Jürgen Fuchs, Bad Emstal (DE); Jürgen Hartung, Helsa (DE); Jürgen Steger, Körle (DE)

(73) Assignee: Braun Melsungen AG, Melsungen (DE)

( * ) Notice: Subject to any disclaimer, the term of this patent is extended or adjusted under 35 U.S.C. 154(b) by 893 days.

(21) Appl. No.: 17/263,254

(22) PCT Filed: Jul. 26, 2019

(86) PCT No.: PCT/EP2019/070214
§ 371 (c)(1),
(2) Date: Jan. 26, 2021

(87) PCT Pub. No.: WO2020/025484
PCT Pub. Date: Feb. 6, 2020

(65) Prior Publication Data
US 2021/0187192 A1    Jun. 24, 2021

(30) Foreign Application Priority Data

Aug. 1, 2018   (DE) .................... 10 2018 118 630.4

(51) Int. Cl.
*A61M 5/145*    (2006.01)
*A61M 5/168*    (2006.01)
(Continued)

(52) U.S. Cl.
CPC ...... *A61M 5/16804* (2013.01); *A61M 5/1452* (2013.01); *A61M 5/1411* (2013.01);
(Continued)

(58) Field of Classification Search
CPC ............ A61M 5/16804; A61M 5/1452; A61M 5/14216; A61M 2205/27; A61M 5/1413; A61M 2005/14573
See application file for complete search history.

(56) References Cited

U.S. PATENT DOCUMENTS 3,985,133 A    10/1976  Jenkins et al.
4,515,591 A *   5/1985  Hemmerich ...... A61M 5/14216
                                                    604/152
(Continued)

FOREIGN PATENT DOCUMENTS

CA    2416286 A1    1/2002
CN    104582755 A    4/2015
(Continued)

OTHER PUBLICATIONS

Office Action received in Chinese Application No. 201980050492.6 dated May 23, 2022, with translation, 16 pages.
(Continued)

*Primary Examiner* — Nathan R Price
*Assistant Examiner* — Haden Matthew Ritchie
(74) *Attorney, Agent, or Firm* — Christopher A. Rothe; CM Law (57) ABSTRACT

An infusion system includes a pump and a replaceable pump module. The pump module can be arranged in a mount of the pump and includes a plunger-barrel unit operatively connectable to a drive mechanism of the pump. The pump module includes a plunger that can be coupled to the drive mechanism by a coupling structure operatively connected to the plunger and a counter-coupling structure for connecting engagement in the coupling structure and operatively connected to the drive mechanism. In a securing position, the infusion system includes a securing member which locks the coupling structure and the counter-coupling structure to each other. In addition or in the alternative, the infusion pump (Continued)

includes a control link operatively connected to the pump module.

13 Claims, 4 Drawing Sheets

(51) Int. Cl.
    *A61M 5/14*            (2006.01)
    *A61M 39/24*          (2006.01)

(52) U.S. Cl.
    CPC ......... *A61M 39/24* (2013.01); *A61M 2205/27* (2013.01); *A61M 2205/505* (2013.01); *A61M 2205/8206* (2013.01); *A61M 2205/8237* (2013.01)

(56) References Cited

U.S. PATENT DOCUMENTS

| | | | |
|---|---|---|---|
| 4,648,872 A | 3/1987 | Kamen | |
| 9,579,455 B2* | 2/2017 | Weber | A61M 5/1456 |
| 10,092,693 B2 | 10/2018 | Hanson et al. | |
| 10,183,113 B2 | 1/2019 | List | |
| 2002/0176788 A1 | 11/2002 | Moutafis et al. | |
| 2005/0020980 A1 | 1/2005 | Inoue et al. | |
| 2011/0150680 A1* | 6/2011 | Dion | F04B 53/147 417/559 |

FOREIGN PATENT DOCUMENTS

| | | |
|---|---|---|
| CN | 105764543 A | 7/2016 |
| DE | 2660392 C2 | 10/1983 |
| EP | 0110276 A2 | 6/1984 |
| WO | 2016176198 A1 | 11/2016 |

OTHER PUBLICATIONS

Search Report received in Chinese Application No. 201980050492.6 dated May 12, 2022, with translation, 5 pages.
German Search Report received in Application No. 102018118630.4 dated Oct. 17, 2018, 9 pages.
International Search Report received in Application No. PCT/EP2019/070214 dated Oct. 24, 2019, 5 pages.
Written Opinion received in Application No. PCT/EP2019/070214 dated Oct. 24, 2019, 18 pages.

* cited by examiner

000
INFUSION SYSTEM HAVING AN INFUSION PUMP AND HAVING A PUMP MODULE THAT CAN BE COUPLED THERETO

CROSS-REFERENCE TO RELATED APPLICATIONS

This is the United States national phase entry of International Application No. PCT/EP2019/070214, filed Jul. 26, 2019, and claims the benefit of priority of German Application No. 10 2018 118 630.4, filed Aug. 1, 2018. The contents of International Application No. PCT/EP2019/070214 and German Application No. 10 2018 118 630.4 are incorporated by reference herein in their entireties.

FIELD

The present invention relates to an infusion system comprising an infusion pump and a replaceable separate pump module, wherein the pump module can be or is disposed in a mount of the infusion pump and comprises/includes a plunger-barrel unit operatively connectable to a drive mechanism of the infusion pump having a plunger which is translationally movable within a barrel, wherein the plunger can be coupled to the drive mechanism by means of a coupling structure operatively connected to the plunger and a counter-coupling structure designed for connecting engagement in the coupling structure and operatively connected to the drive mechanism.

BACKGROUND

In infusion technology, peristaltic pumps as well as syringe pumps are generally known to supply a patient with liquid. For applications making high requirements regarding the dosing accuracy usually syringe pumps are employed, as the latter allow for properly and accurately achieving defined fluid delivery. For applications requiring larger fluid delivery volume, peristaltic pumps are properly suited as they deliver largely continuously and without any discrete delivery volume due to their delivery technology.

From the state of the art, applications of an infusion pump are known in which relatively large delivery volumes have to be paired with high delivering accuracy, which entails big problems. Syringe pumps show the drawback that the fluid volume to be delivered by said pumps is limited, i.e. by the volume of the syringe used (cylinder volume). Although peristaltic pumps, on the other hand, can provide relatively large delivering volumes, they have the drawback of a low delivering accuracy as compared to the syringe pump. In particular, in the case of low delivery rates the delivering accuracy thereof is not ensured due to the usually employed peristaltic system of the tube. Moreover, the drive of a peristaltic pump usually is relatively large and heavy and is relatively energy-consuming due to the flexing of the pump tube by the peristaltic drive.

The afore-described problems are solved by an infusion system to the applicant in which a pump module comprising a plunger-barrel unit is provided which is adapted to be operated by means of a drive mechanism of the infusion pump, wherein a valve unit is provided to interrupt, in the case of a pump delivery stroke, connection between the plunger-barrel unit as intermediate liquid reservoir and a supply port to a separate large fluid volume as well as to release connection between the plunger-barrel unit and a patient port and to release, in the case of a pump suction stroke, the connection between the plunger-barrel unit and the supply port to the separate large fluid volume as well as to block the connection between the plunger-barrel unit and the patient port. The pump module designed as disposable and formed separately from the infusion pump is replaceably arranged in the multi-use infusion pump, thus offering especially for home infusion systems inter alia the great advantage that the sterility during infusion can be easily safeguarded. However, further important aspects have to be observed when an infusion is administered and when the infusion system is utilized, such as e.g. the fact that malfunctions and maloperations of the system can be preferably completely excluded and that a course of treatment as intended can be guaranteed.

SUMMARY

Based on the afore-explained problems, the object underlying the invention is to eliminate the afore-listed drawbacks, especially to provide an infusion system which enables an especially simple user-friendly and safe coupling of the pump module to the infusion pump and ensures the system to be started not before the pump module is coupled to the infusion pump as intended (i.e. is correctly inserted in the mount on the side of the infusion pump) and ensures the system preferably not to be just shut down during ongoing treatment.

In a first aspect, the invention relates to an infusion system comprising an infusion pump and a replaceable pump module separate herefrom, wherein the pump module can be/is arranged in a mount of the infusion pump and comprises a plunger-barrel unit operatively connectable to a drive mechanism of the infusion pump and having a plunger translationally movable within a barrel, wherein the plunger can be coupled to the drive mechanism by means of a coupling structure operatively connected to the plunger and a counter-coupling structure designed for connecting engagement in the coupling structure and operatively connected to the drive mechanism, the infusion system including a securing member which in a securing position interlocks the coupling structure and the counter-coupling structure in the coupled state.

In a second aspect (which may be combined with the first aspect), the invention relates to an infusion system comprising an infusion pump and a replaceable pump module, wherein the pump module can be arranged in a mount of the infusion pump and comprises a plunger-barrel unit operatively connectable to a drive mechanism of the infusion pump and having a plunger translationally movable within a barrel, wherein the plunger can be coupled to the drive mechanism by means of a coupling structure operatively connected to the plunger and a counter-coupling structure designed for connecting engagement in the coupling structure and operatively connected to the drive mechanism, the infusion pump including a control link which is operatively connected to the pump module so that, when the pump module is arranged in the mount as intended, it is positioned by force into a release position or pump position or infusion position in which pumping action of the plunger is possible, and that, unless the pump module is arranged in the mount as intended, it is positioned by force into a blocking position or uncoupling position in which pumping action of the plunger is not possible.

In a third aspect (which may be combined with the first and/or second aspect), the invention relates to an infusion system comprising an infusion pump and a replaceable pump module, wherein the pump module is adapted to be arranged in a mount of the infusion pump and comprises a plunger-barrel unit operatively connectable to a drive mechanism of the infusion pump and having a plunger translationally movable within a barrel, wherein the plunger can be coupled to the drive mechanism by means of a coupling structure operatively connected to the plunger and a counter-coupling structure designed for connecting engagement in the coupling structure and operatively connected to the drive mechanism, wherein the infusion system includes a securing member which in a securing position interlocks the coupling structure and the counter-coupling structure in the coupled state and the infusion pump including a control link which is operatively connected to the pump module so that, when the pump module is arranged in the mount as intended, it is positioned by force into a release position, wherein the infusion system includes a securing member which in a securing position interlocks the coupling structure and the counter-coupling structure in the coupled state.

One preferred embodiment of the infusion system is characterized in that the infusion pump includes a cover member. The latter may be positioned especially into a closing position closing the mount for the pump module (and into an open position releasing the mount). The cover member, the mount and the pump module are preferably adapted to each other and configured such that, when the pump element is not arranged in the mount as intended, the cover member cannot be positioned into the closing position closing the mount. In this way, prior to starting the pump the user receives feedback about whether or not the pump module is correctly arranged in and connected to the infusion pump.

In another preferred embodiment, the cover member is operatively connected to the control link. The operative connection is preferably designed so that it is positioned by force into the release position when the cover member is in the closing position and it is positioned by force into the blocking position when the cover member is not in the closing position. The operative connection may be realized especially by a mechanism, especially a toggle lever mechanism. The latter may include especially a first lever arm and a second lever arm which are connected to each other via a free joint. Either of the lever arms may be substantially L-shaped. Moreover, either of the lever arms may be pivotally arranged at the infusion pump, especially by means of a fixed pivot joint arranged at the housing thereof. The toggle lever mechanism may further be coupled to an operating rod (cams or the like) interacting with the cover member. The remaining one of the two lever arms is preferably rotatably coupled to the control link by its end opposed to the other lever arm.

According to another preferred embodiment, the securing member which may especially be in the form of a preferably substantially hollow-cylindrical clamping sleeve is operatively connected to the control link. Said operative connection is preferably configured so that the securing member fixes the coupling structure and the counter-coupling structure when the control link is in the release position and the securing member releases the coupling structure and the counter-coupling structure when the control link is in the blocking position. For example, the control link may include a control groove. Preferably, the latter comprises a release portion extending in the longitudinal direction L and a blocking portion being first inclined and then extending transversely to the longitudinal direction L. The securing member in this case includes at least one, preferably two diametrically opposed control cams engaging in the control groove of the control link so that the securing member can be positioned by relative positioning of the control link due to the afore-described engagement between a securing position or clamping position and a release position.

One preferred embodiment of the invention is characterized in that the infusion system, especially the infusion pump, includes a toggle lever mechanism. On the one hand, the latter is operatively connected to the pump module, especially via coupling to the cover member. On the other hand, it is operatively connected to the control link, for example by being articulated to the control link.

The control link may be biased especially into the blocking position/uncoupling position, e.g. by means of a spring element such as a flexural spring, compression spring or tension spring. In this way, pumping action is ensured to be impossible unless the pump module is connected as intended.

According to a preferred embodiment of the invention, the securing member is a sleeve-shaped hollow body. The longitudinal axis of the securing member/hollow body is aligned preferably in parallel to, is especially congruent to the plunger axis. Further, the securing member can be positioned between the securing position and a release position preferably relative to the coupling structure and the counter-coupling structure in the direction of the plunger axis.

The securing member is preferably biased into the securing position, for example by means of a spring element such as a flexural spring, compression spring or tension spring. In this way, the pump module is ensured, when arranged in the mount of the infusion pump as intended, to be constantly safely coupled to the drive thereof and inadvertent release is ensured to be safely prevented.

The drive of the infusion pump may especially include a drive rod and a coupling rod and may be adapted to be operatively coupled by the latter to the plunger of the plunger-barrel unit. Of preference, all of said members are disposed in the direction of the longitudinal axis of the plunger-barrel unit. The drive rod and/or the coupling rod may be permanently coupled to each other and to the drive. Hence, they are not intended to be uncoupled from the drive by a user. The drive rod is preferably translationally driven and, consequently, may reciprocate in the direction of the longitudinal axis L. The coupling rod may include, at its distal end, a counter-coupling structure which is designed to match the coupling structure of the plunger. The counter-coupling structure may especially have a possibly peripheral deepening or groove which is suited and intended for coupling engagement in coupling hooks of the plunger. The securing member preferably can be positioned relative to the coupling rod in the direction of the longitudinal axis L between a distal clamping position and a proximal release position. In the clamping position it engages the meshing coupling structure and counter-coupling structure so that they cannot disengage from each other and the connection of plunger/pump module and drive/infusion pump is secured. In the release position, the securing member releases the coupling structure and the counter-coupling structure so that a user can easily remove the pump module from the mount.

An especially user-friendly and safe embodiment of the infusion system is preferably characterized in that it has an emergency release by an actuating member coupled to the securing member. By means of the actuating member the securing member can be manually operated and can be moved or transferred from the securing position to a release position. It is of particular advantage when the actuating member is coupled to the control link so that, when the control link is in the release position, it blocks and cannot be actuated for moving the securing member from the securing position to a release position. In this way, the pump module and the infusion pump can be safely prevented from being uncoupled during use due to inadvertent actuation of the emergency release.

The mount of the infusion pump for the pump module can be in the form of a recess in a pump housing, for example, and can be closed especially by means of a cover member or closure (e.g. in the form of a cover flap pivotally disposed at the pump, especially at the housing thereof). The cover member can be lockable to the housing part especially in a position closing the mount via a locking unit. The closure, the mount and the pump module may be adapted to each other so that closing (and locking, where necessary) of the closure is possible only when the pump module is correctly arranged and connected as intended. Thus, feedback may be provided to a user with respect to faultless implementation and use of the pump, which advantageously increases safety of the patients.

In addition, by closing the cover member automatic coupling of the plunger-barrel unit to the drive can be effectuated which constitutes especially simple and safe operation. A housing of the infusion pump may consist especially of a lower housing part on which the entire mechanics and electronics may be disposed and retained, as well as of an upper housing part which may include especially a display and various switching elements. Inside the housing a locking mechanism for the cover flap may be provided.

The plunger may be disposed especially at a coupling rod, especially preferred at an end of the coupling rod facing the two tube portions. The other end of the coupling rod may protrude from the barrel. The plunger may especially be longer than the maximum fill level of the barrel. In this way, ambient air which is naturally outside the barrel is prevented from mixing with the medium present within the barrel. The combination of two sealing lips and plunger/barrel length results in an efficient barrier against penetrating germs. Of preference, the two-sided sealing of the plunger of the plunger-barrel unit is realized by means of a proximal seal and a distal seal. Thus, a vacuum movement and an excess pressure movement of the plunger is sealed to ensure sterility of a fluid compartment/dosing compartment, i.e. of the compartment in which the fluid to be delivered is present in the barrel. In this way, the pump meets the high requirements regarding cleanliness in the medical environment. The proximal seal and the distal seal are advantageously plane-parallel to each other. Since the plunger has a substantially circular cross-section, approximately annular seals are resulting herefrom. The distance between the proximal seal and the distal seal is especially larger than the delivery stroke of the plunger-barrel unit. It is resulting herefrom that the dosing area contacts exclusively the plunger and the sterile sealing lip thereof, thus constructively preventing the fluid compartment/dosing compartment from being stained/polluted due to excessive stroke movements.

According to a preferred embodiment, the plunger-barrel unit includes a coupling member for releasably coupling to a corresponding counter member of a drive of the infusion pump. Said coupling member may be arranged or formed directly at the plunger. The coupling member may be in the form of a plug coupling matching the counter-coupling structure, for example, and may be coupled automatically or forcedly to the drive when the pump module is arranged in the infusion pump as intended. Preferably, the coupling includes engaging structures holding both coupling members adjacent to each other and especially enable the two coupling members to engage in a way which a user can hear and/or feel.

The plunger-barrel unit preferably is a smooth-running unit to minimize operating forces and to achieve high delivering accuracy. This can be achieved, for example, by providing seals on both sides of the plunger in the axial direction and thus sealing the plunger against the barrel. Especially, the plunger-barrel unit may be in the form of a syringe having a smooth-running plunger which exhibits sealing contours in the push and pull direction. This allows using the plunger while maintaining the sealing effect in both directions of movement.

The drive mechanism of the infusion pump may consist especially of an electric drive motor and a transmission gear for transforming the movement of rotation of the drive motor into a translational movement (reciprocal movement) of the plunger movably supported in the barrel. Moreover, the drive mechanism may be controlled/regulated e.g. via a control/regulating unit of the infusion pump.

In one embodiment, the infusion pump may comprise a valve unit which is connected e.g. to the control/regulating unit and is arranged to interrupt (possibly in a regulated/controlled manner), in the case of a pump delivery stroke, a connection between the plunger-barrel unit as intermediate fluid reservoir and a supply port to a separate large fluid volume as well as to release a connection between the plunger-barrel unit and a patient port and, in the case of a pump suction stroke, to release the connection between the plunger-barrel unit and the supply port to the separate large fluid volume as well as to block the connection between the plunger-barrel unit and the patient port. In the simplest case, the valve unit may include passively operable valve members, for example one or two check valves, which are accommodated in connecting lines, especially in separate connecting lines in the form of disposables, to the patient port and to the large fluid volume which can be inserted into the infusion pump. This offers the advantage that the valve unit can be manufactured at particularly low cost and thus can be disposed of as disposable together with the entire fluid line system.

As an alternative, the valve unit may include actively operable valve members, for example two tube pinching/pressing units adapted to act on flexibly deformable portions of the two connecting lines for pinching the same in a sealing manner. Said valve members may be accommodated especially in the infusion pump (or the pump module). In particular, the fluid line system in the form of a disposable, where appropriate, may have a first, preferably elastically deformable tube portion for fluid supply (from the large fluid reservoir into the intermediate reservoir) and a second preferably elastically deformable tube portion for fluid discharge (from the intermediate reservoir toward the patient), the two tube portions being designed for insertion into the infusion pump and for connection to the plunger-barrel unit (intermediate fluid reservoir) for sucking fluid from the first tube portion into the intermediate fluid reservoir and for discharging fluid from the intermediate fluid reservoir to the patient. The tube pinching/pressing units may preferably be rams/punches or shear clamps or similar mechanical clamping means which are movably supported in the infusion pump (thus are part of the infusion pump) and can be operated by a respective drive connected to the control/regulating unit. The two tube pinching/pressing units present in the inlet and in the outlet are preferably mechanically coupled to each other so that at least one side safely pinches the tube. In order to prevent any leakage from occurring when it is changed between the inlet and the outlet, the tube pinching/pressing units may be biased so that they bridge the otherwise leaky positions. Alternatively, the valves can be controlled in time also via cam disks or by being separately controlled by means of motors, for example.

Via the control unit which may be realized e.g. in the form of a motor-driven valve control, the tube outlet, viz. the second tube portion, can be blocked, preferably pinched, when the plunger-barrel unit is attached. In addition, the tube inlet, viz. the first tube portion, can be blocked, preferably pinched, when the plunger-barrel unit is ejected. It is significant that the plunger-barrel unit can be controlled like a reciprocating plunger pump. The control unit may especially include a motor-driven tilt lever unit. The latter may be configured and act in such a way that in a first tilting position it squeezes the first tube portion and releases the second tube portion and in a second tilting position it squeezes the second tube portion and releases the first tube portion. The control unit may further include a ram arranged pivotally at the tilt lever unit. It may comprise, above all, an inlet ram interacting with the first tube portion and/or an outlet ram interacting with the second tube portion. At least one shoe can be biased by means of a biasing unit, especially by means of a compression spring, into an especially non-contacting position which releases the respective tube portion. In this manner, the shoes can be prevented from being present in the area of the respective tube portion when the pump is not operative. This enables the pump module according to the invention to be replaced, inserted and removed in an especially user-friendly manner.

One preferred embodiment of the pump module provides the first tube portion to be equipped with a Luer lock coupling member at the end opposed to the plunger-barrel unit. It may be especially a Luer lock internal taper. Alternatively, or additionally, the second tube portion may be provided with a Luer lock coupling member at the end opposed to the plunger-barrel unit. This may especially be a Luer lock external taper. This permits especially easy connection of the pump module and, resp., the fluid line system accommodated in the latter to an extracorporeal line or line system. Consequently, the invention can be used easily and in a known way together with existing and wide-spread medical equipment. Alternatively to a Luer lock connection, a drip chamber connected to the patient may be provided or the second tube portion is in the form of a bag line having a closed end and can be connected by an insertion mandrel. In addition, or as an alternative, it is also an option to arrange a spike/piercing mandrel to increase the flexibility in the field of application and, resp., the compact design of the pump.

The control unit and the drive can be arranged especially at or in a housing part of the infusion pump.

The pump module may be arranged at the housing part to be especially replaceable by the user. It has to be arranged in the pump and/or to be removed from the pump preferably without making use of any specific tools or devices. The pump module according to the invention may be especially a disposable and may be intended for one single use in the pump. This is especially advantageous and user-friendly with respect to sterile conditions. It may be realized, for example, in the form of a disposable syringe by the delivery volume opening of which the two tube portions are fluid-connected. This may be realized by the fact that the two tube portions form a continuous fluid line which is provided with a branch for connecting the plunger-barrel unit, especially a disposable syringe, in an area between the deforming points. Alternatively, the plunger-barrel unit/the disposable syringe may have two flow openings, one outlet and one inlet, each of which is fluid-connected to the corresponding tube portion.

It is of particular advantage when the drive of the plunger-barrel unit is a linear drive/motor disposed in the axis of movement of the plunger. It is especially preferred when the drive is arranged and configured so that forces acting from the drive upon the plunger are transmitted centrally and in the axial direction. It is especially advantageous that forces acting on the plunger can be minimized (as compared to a decentralized force transmission) and thus only low energy is required to actuate the plunger-barrel unit. As a consequence, the drive and thus the pump may be small, which results in savings regarding weight, costs and construction space. Moreover, high precision can be achieved by central transmission of actuating forces to the plunger. The use of a small syringe as a plunger-barrel unit enables a linear drive to be arranged directly in the axis of the syringe plunger, thus preventing any transverse forces affecting the accuracy from acting on the syringe plunger. Further, a small cross-section of the syringe generates low forces only, which permits using a simple low-cost drive, for example a linear step motor. The construction size of the pump thus may be significantly smaller than in known infusion pumps.

The infusion pump may additionally include a second drive, especially a linear drive/motor, for the control unit. The two drives for the plunger-barrel unit and the control unit are preferably coupled in terms of control so that the afore-described control function is carried out by pinching the two tube portions.

Since the drive/drives of the pump may be designed to be small, it is advantageously possible for the pump to comprise an energy storage unit, especially a battery, and to be operated without any direct mains connection. The energy storage unit may be e.g. a common lithium battery which can be charged via USB interface. The latter may further be used to read data into and/or out of a pump controller.

The pump module may include a shift clamp which can be adjusted so that it optionally releases or blocks fluid flow in the first and/or second tube portion. In this way, the shift clamp can be adjusted so that after starting up the pump module no air bubbles will form. The shift clamp preferably can be clipped onto a handle portion of the pump module so that it can simply be made from a material different from that of the remaining pump module. A sleeve/ring may be disposed at an end of the pump module or, resp., of the handle portion facing away from the shift clamp. Said sleeve is suited for fixing the first and/or second tube portion and thus to allow for safe coupling of an infusion line to the pump module. Consequently, it serves as a retaining ring through which the infusion line can be threaded.

Summing up, it can be stated that the invention enables an infusion system exhibiting the accuracy of a syringe pump and the delivery volume or volume storage of a peristaltic pump with significantly lower energy required, reduced construction space and low manufacturing costs while the user friendliness and the safety are high. The following advantages can especially be achieved by the invention:
  easier operation for the user
  the system permits operation of the pump in the case of correct application only.

BRIEF DESCRIPTION OF THE DRAWING FIGURES

Further features and advantages of the invention will be resulting from the following exemplary and non-limiting description of the figures. They are merely schematic and serve only for the comprehension of the invention, wherein.

DETAILED DESCRIPTION

Figure 1:
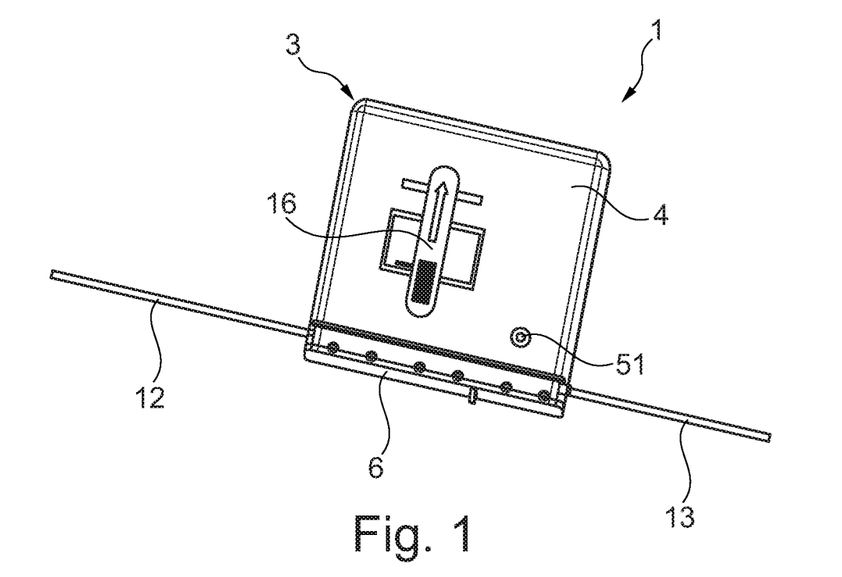
FIG. 1 shows a perspective view of the rear side of an infusion system comprising an infusion pump and a pump module inserted in the latter.
Figure 6:
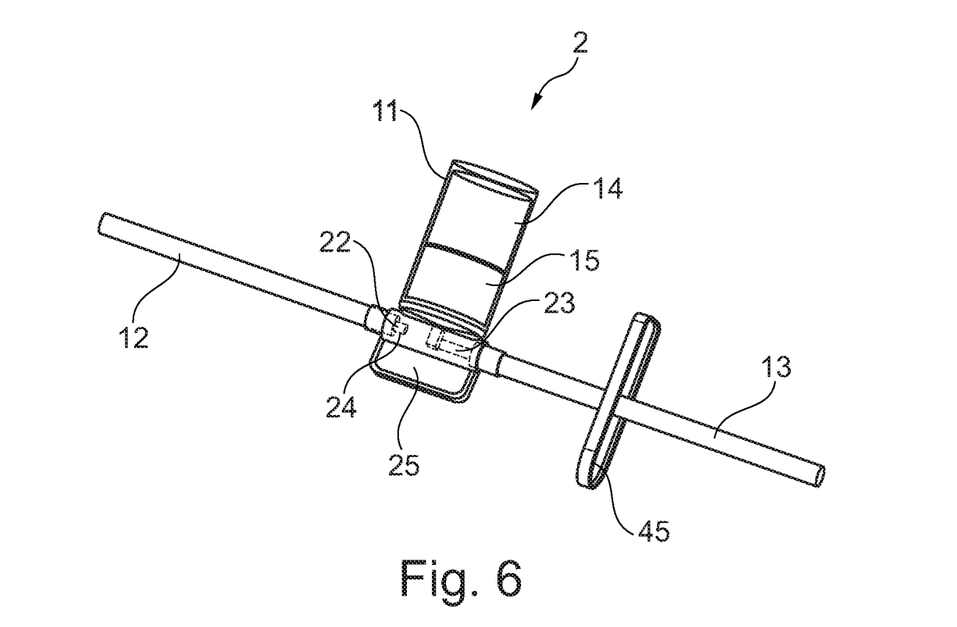
FIG. 6 shows an embodiment of the pump module with a connected shift clamp for squeezing one of the fluid lines.
Figure 7:
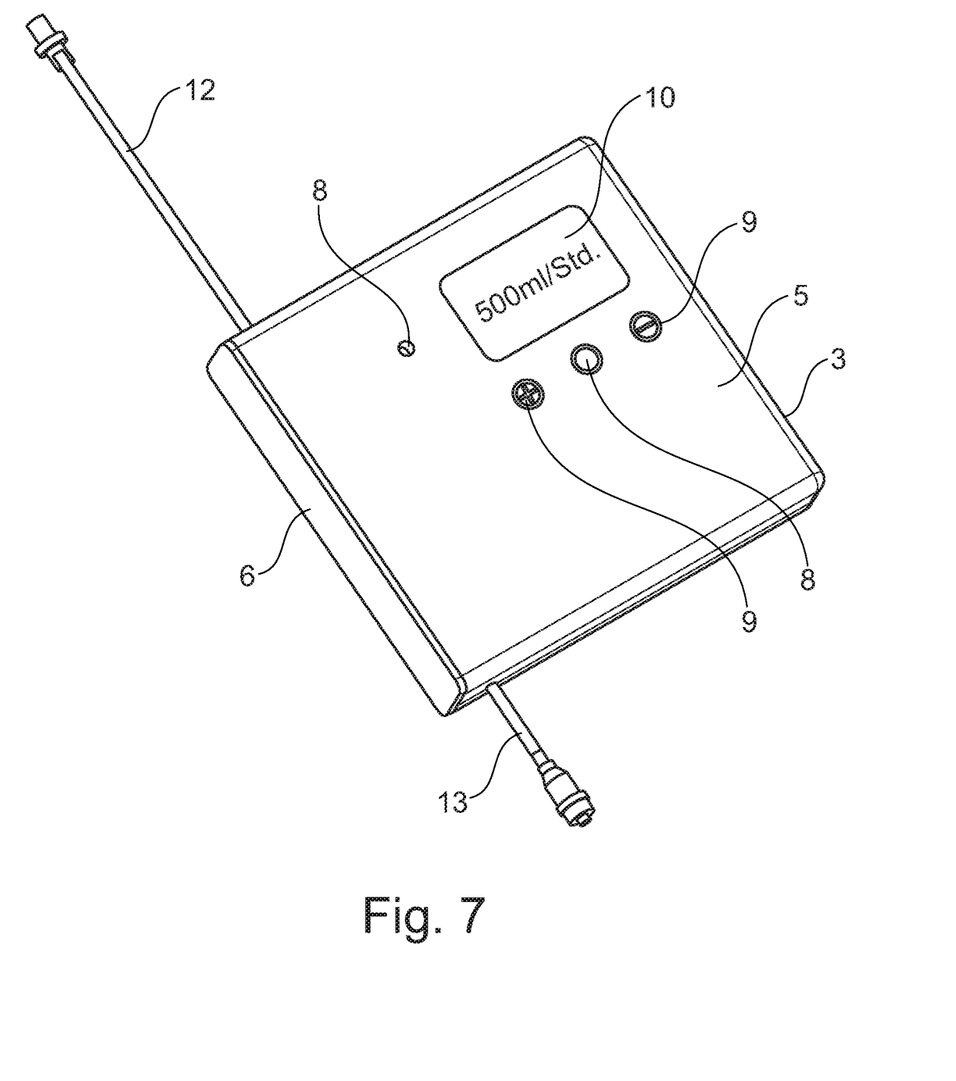
FIG. 7 shows a perspective view of the front side of an infusion system comprising an infusion pump and a pump module inserted in the latter.

FIGS. 1 and 7 illustrate an exemplary embodiment of an infusion system according to the invention comprising an infusion pump 1 and comprising a pump module 2 inserted in the latter (FIG. 1 rear side, FIG. 7 front side). The pump 1 includes a housing 3 which preferably consists substantially of a lower housing part 4 including a housing cover 5 and a cover member 6 in the form of a cover flap 6 here. The lower housing part 4 and the housing cover 5 are connectable/connected to each other, for example via a locking connection or screwed connections not shown in the Figures, and in the assembled state form the housing 3. The lower housing part 4 has a housing bottom 7. In or at the housing cover 5 display elements 8, operating elements 9 and a display 10 of the pump 1 are disposed. In the lower housing part 4 an actuating element 16 is arranged in the form of a shift latch 16 in this case. In the housing 3 a mount 30 for the pump module 2 is configured (see especially in FIG. 2) which can be closed by means of the cover member 6. The mount 30 is open in the distal direction, is closed in the proximal direction by means of a bottom wall 32 and is enclosed by a sidewall 33 (sidewalls 33) corresponding to the external shape of the plunger-barrel unit. In total, the mount 30 is formed to match the plunger-barrel unit 11 (shown in FIG. 6) so that the latter can be arranged therein in a defined position. In the bottom wall 32 of the mount 30 a central through-hole is formed through which a coupling rod 38 and a clamping sleeve 39 as a securing member 39 are passed for coupling the plunger 15 to the drive 26, as will be described below.

Figure 4:
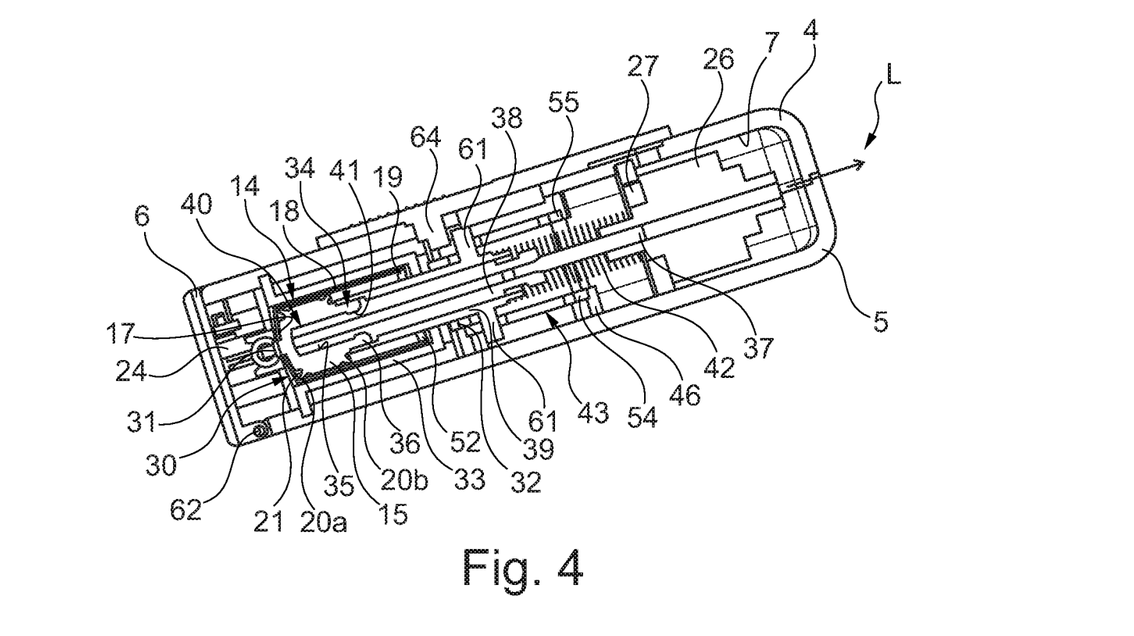
FIG. 4 shows a sectional view transversely to the section plane of FIGS. 2 and 3 of the infusion pump with a pump module inserted therein.
Figure 5:
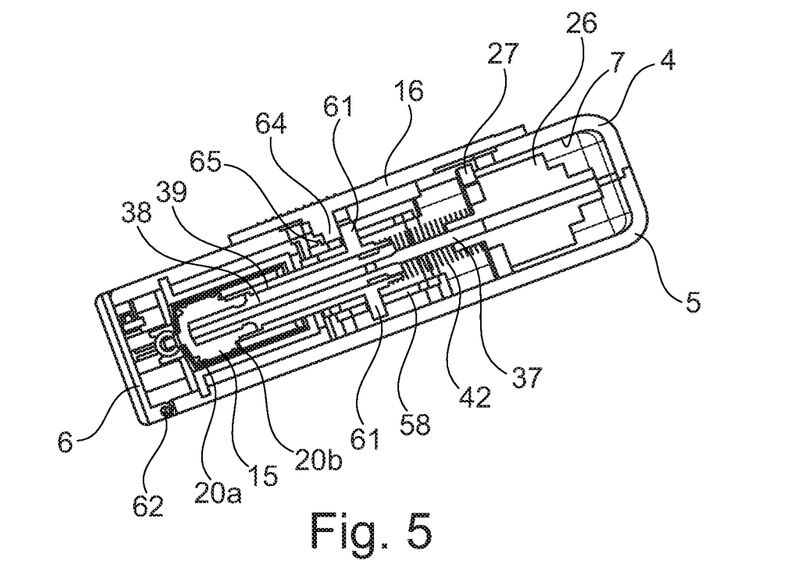
FIG. 5 shows another sectional view transversely to the section plane of FIGS. 2 and 3 of the infusion pump with an inserted pump module during actuation of an emergency release.

The pump module 2 is schematically shown separately in FIG. 6. A more detailed representation of the pump module 2 is found in FIGS. 3, 4 and 5. It includes a plunger-barrel unit 11, a first elastically deformable tube portion 12 and a second elastically deformable tube portion 13. The pump module 2 is in the form of a single-use article (disposable). The tube portions 12, 13 may especially be configured as a PVC tube.

The plunger-barrel unit 11 includes a barrel 14 which may be made especially from plastic material and/or may be manufactured as an injection-molded part, and includes a plunger 15 to be reciprocated therein which may equally be made especially from plastic material and/or may be manufactured as an injection-molded part. The barrel 14 includes a bottom wall 17, a circumferential wall 18 and a cover wall 19. The plunger 15 is sealed against the circumferential wall 18 by means of seals 20a, 20b arranged on both sides so that the plunger-barrel unit 11 has a fluid compartment/dosing compartment 21. The plunger 15 has a coupling structure 34 on its proximal side, i.e. on the side opposed to the fluid compartment 21. Said coupling structure is formed by a central blind hole 35 introduced to the plunger 15 at the proximal edge of which coupling hooks 36 provided with locking contours are disposed. In the bottom wall 17 a fluid passage 31 is formed. The plunger-barrel unit 11 includes at its distal end area a barrel head 24 at which in turn a handle member 25 is distally arranged for user-side handling of the pump module 2, especially when inserting the infusion pump 1 into or removing the infusion pump 1 from the mount 30. An annular bead 52 located in the side wall 18 constitutes an axial stop for the plunger 15 so that the maximum stroke of the plunger-barrel unit 11 is fixed and the plunger 15 is form-fit prevented from falling out of the barrel 14.

The plunger 15 is preferably arranged/formed/fixed as a smooth-running plunger and at its distal end and at its proximal end includes a seal 20a, 20b in the form of a movable sealing lip. The distance along the longitudinal direction L between the distal seal 20a and the proximal seal 20b of the plunger 15 exceeds the plunger stroke of the plunger-barrel unit 11 in the shown exemplary embodiment. This guarantees that the barrel wall of the fluid compartment dosing compartment 21 contacts exclusively the one distal seal 20a so that the sterility thereof is safeguarded. Preferably, the excess between the distance along the longitudinal direction L between the distal seal 20a and the proximal seal 20b of the plunger 15 and the plunger stroke amounts to at least 2 mm.

In the barrel head 24 an inlet bore 22 and an outlet bore 23 are formed (cf. FIG. 6) which are fluid-connected, on the one hand, to the fluid passage 31 and are fluid-connected, on the other hand, to the first tube portion 12 and the second tube portion 13. In this way, the fluid compartment 21 is fluid-connected via the fluid passage 31 and the inlet bore 22 to the first tube portion 12 and is fluid-connected via the fluid passage 31 and the outlet bore 23 to the second tube portion 13. The tube portions 12, 13 may be molded especially onto the barrel 14 and, resp., the barrel head 24. They may be configured especially like common infusion tubes. The first tube portion 12 is provided, in the embodiment of FIG. 3, with an inlet Luer lock connection (not shown) at its end facing away from the plunger-barrel unit 11. The second tube portion 13 is provided with an outlet Luer lock connection (not shown) at its end facing away from the plunger-barrel unit 11. In this way, the pump module 2 can be easily connected to common infusion units.

FIGS. 2 to 5 show that the pump 1 includes a drive 26 for the plunger-barrel unit 11 (inherent to the pump), here in the form of a linear motor 26. The motor 26 is arranged to be congruent to the longitudinal axis L of the plunger-barrel unit 11 so that forces for reciprocating the plunger 15 can be transmitted centrally and without any twists/transverse forces. The drive 26 is arranged to be fixed in position at the lower housing part 4 by being mounted in an intermediate wall 27.

The drive 26 can be operatively coupled to the plunger 15 via a drive rod 37 and a coupling rod 38. Both the drive rod 37 and the coupling rod 38 are constituent parts of the infusion pump 1 and are coupled permanently to each other and to the drive motor 26, viz. are not intended to be uncoupled from the latter by a user. The drive rod 37 is driven by means of the drive motor 26 and therefore may perform a reciprocating movement in the direction of the longitudinal axis L. At its distal end, the coupling rod 38 has a counter-coupling structure 40 which is formed to match the coupling structure 34 of the plunger 15. The counter-coupling structure 40 here is provided in an area of reduced diameter with a possibly peripheral deepening 41 or groove 41 which is suited and intended for coupling engagement in the coupling hooks 36 of the plunger 15.

On the coupling rod 38 a securing member 39, here in the form of a clamping sleeve 39, is arranged to be positioned relative to the coupling rod 38 in the direction of the longitudinal axis L between a distal clamping position and a proximal release position. In the clamping position (see FIG. 4), the clamping sleeve 39 engages the coupling hooks 36 engaging in the deepening 41 by its distal end portion so that the coupling hooks cannot detach from the deepening by deformation radially outwardly and the connection of the coupling structure 34 and the counter-coupling structure 40 is secured. In the release position (FIG. 5), the distal end portion of the clamping sleeve 39 releases the coupling hooks 36 so that they can deform outwardly in the radial direction and can detach from the deepening 41, when a user seizes the pump module 2 at the handle member 25 and removes the same from the mount 30 in the distal direction. The clamping sleeve 39 is biased into the distal direction, viz. into its clamping position, by means of a compression spring 42.

Figure 2:
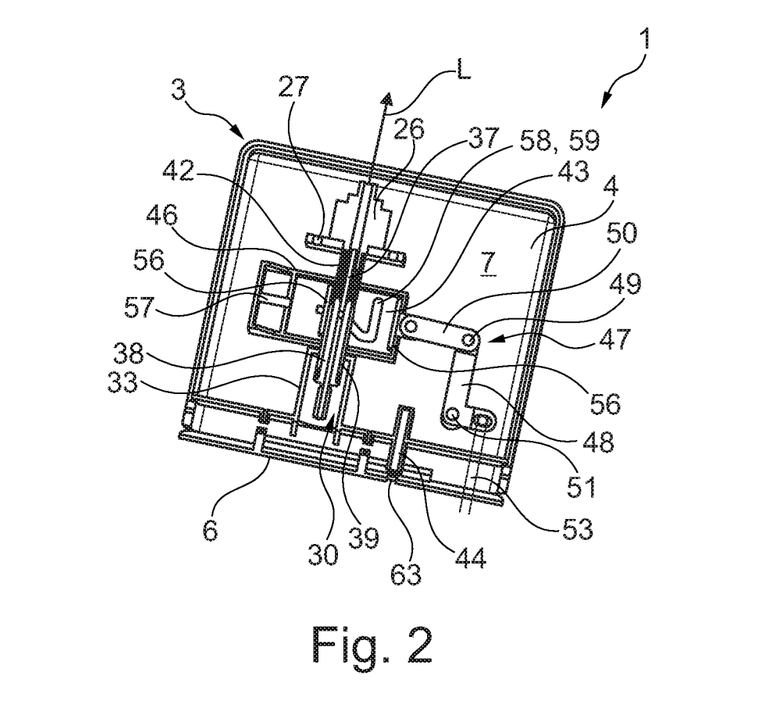
FIG. 2 shows the infusion system of FIG. 1 in a sectional view, while the pump housing is partially cut free, in a coupling position or infusion position.
Figure 3:
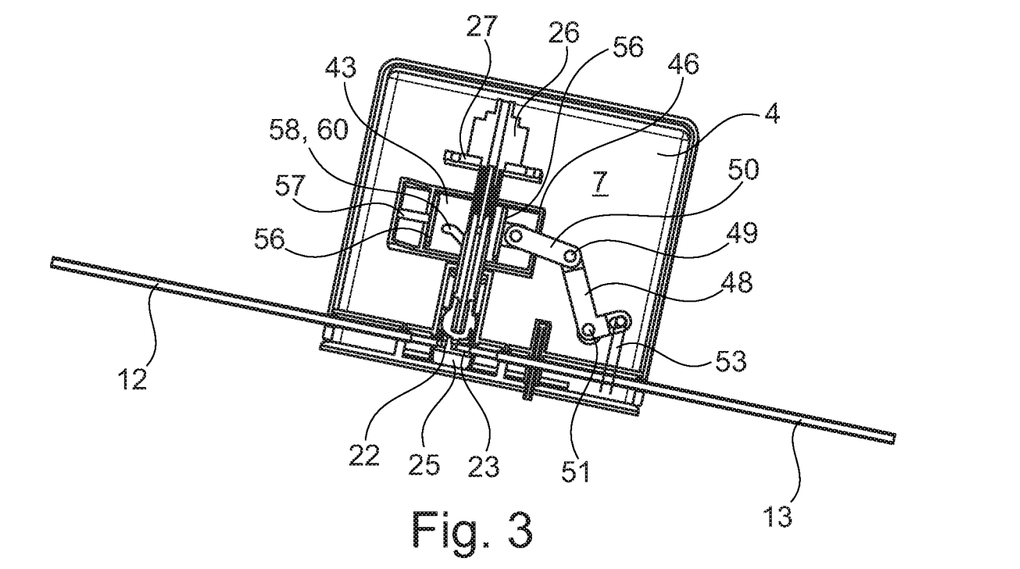
FIG. 3 shows a sectional view of the infusion pump of FIGS. 1 and 2 with a pump module inserted in the same in an uncoupling position.

The infusion pump 2 moreover includes a control link 43. The latter is received to be positioned within a frame 46 of the lower housing part 4 in a direction transversely to the longitudinal direction L between an uncoupling position/blocking position (FIG. 2) and a release position/pumping position (FIG. 3). The control link 43 is coupled to a toggle lever mechanism 47 substantially consisting of a first lever arm 48 and a second lever arm 50 connected to the latter via a free joint 49. The first lever arm 48 is substantially L-shaped and is pivotally arranged at the lower housing part 4 by means of a pivot joint 51 fixed relative to the lower housing part 4. It is coupled by its end opposed to the free joint 49 to an actuating rod 53 interacting with the cover member 6. The second lever arm 50 is rotatably coupled to the control link 43 by its end opposed to the free joint 49.

The control link 43 has a lower wall 54 on the side of the lower housing part, an upper wall 55 on the side of the upper housing part opposed to the lower wall and two sidewalls 56 connecting the upper wall 55 and the lower wall 54. The second lever arm 50 is coupled to the one sidewall 56, while the other sidewall 56 is coupled to a compression spring 57 bearing against the frame 46, the compression spring biasing the control link 43 in the direction of the second lever arm 50 (in the FIGS. 1, 2 and 3 to the right, in the FIGS. 4 and 5 out of the projection plane). In the lower wall 54 (and identically in the upper wall 55) a control groove 58 is configured. It includes a release portion 59 extending in the longitudinal direction L (cf. FIG. 2) and a blocking portion 60 extending initially tilted and then transversely to the longitudinal direction L (see FIG. 3).

The clamping sleeve 39 includes two diametrically opposed control cams 61 engaging in the control grooves 58 of the upper wall 55 and the lower wall 54.

It is resulting from FIGS. 2 to 5 that the cover element 6 in the form of the cover flap 6 is arranged to be pivoting between an opened position (FIG. 3) and a closed position (FIGS. 2, 4 and 5) by means of a hinge joint 62 at the lower housing part 4. Said hinge joint is provided with a positioning pin 63 which interacts with the second tube portion 13 and ensures the latter to be placed at an air sensor 44 as intended when the cover flap 6 is closed.

For using the pump 1 a user first opens the cover flap 6 of the pump 1, for example by inserting a special wrench laterally into a dedicated bore and thus unlocks the cover flap 6. When the front flap 6 is opened, the control link 43 is provided in the uncoupling or blocking position and the coupling rod 38 is provided in the extended state. Thus, the actuating rod 53 has been shifted outwardly (distally) by means of the two lever arms 48, 50. When the infusion line including the two tube portions 12, 13 is filled free from air bubbles, the second tube portion 13 is closed in a fluid-tight manner by means of a shift clamp 45. Then the user shifts the pump module 2 into the intended mount 30 of the pump 1 which in the condition shown in FIG. 2 is provided with the control link 43 in the uncoupling or blocking position (shifted to the right in FIG. 2) and with the clamping sleeve 39 in the release position (shifted to the proximal direction) until the coupling structure 34 engages in the counter-coupling structure 40, i.e. the coupling hooks 36 engage in the deepening 41 preferably in an audible and/or feelable manner and the plunger-barrel unit 11 is connected to the drive 26.

After that, the cover flap 6 is closed. In so doing, the cover flap 6 interacts with the actuating rod 53 and shifts the latter in the proximal direction. As a consequence, the first lever arm 48 carries out a pivoting movement (anti-clockwise in FIGS. 2 and 3) about the fixed pivot joint 51, which causes the control link 43 to be moved against the bias of the compression spring 57 within the frame 46 by means of the second lever arm 50 (from the blocking position shown in FIG. 2 to the left into the release or pumping position shown in FIG. 3). The clamping sleeve 39 is moved, by means of the control cams 61 engaging in the control groove 58, in the distal direction into its clamping position in which the coupling structure 34 and the counter-coupling structure 40 are secured relative to each other. The compression spring 42 located at the clamping sleeve 39 ensures safe connection during operation.

A locking mechanism located in the upper housing part 5 ensures safe locking of the flap 6 in the closed position. At the same time, the second tube portion 13 is placed toward the air sensor as intended and, for example, is pressed against the same. This ensures detection and appropriate communication of possibly present or introduced air bubbles during infusion.

Now the user enters the desired delivery rate via the display elements 8 and the operating elements 9. The delivery rate is shown on the display 10 which may be a touch screen according to one embodiment so that input may also be carried out via the display 10 (operation via a cell phone or tablet App is further possible and is within the scope of the invention). Directly after release the pump 1 will start. As soon as the user has started the infusion, the drive rod 37 of the linear motor 46 will reciprocate with the coupled coupling rod 38 including the clamping sleeve 39 and the plunger 15 within the release portion 59 of the control groove 58 of the control link 43 and, in so doing, will pump infusion solution in the direction of the patient.

After completion of the infusion, the pump 1 is turned off. The drive rod 37 of the linear motor 46 returns the coupling rod 38 with the plunger 15 to the starting position. As soon as the user opens the cover member 6, the compression spring 57 forces the control link 43 back in the direction of the blocking position (to the right in FIGS. 2 and 3). The actuating rod 53 is moved outwardly (distally) again via the toggle mechanism 47. By moving the control link 43 back into the blocking position, as the control cams 61 engage in the control groove 58 the clamping sleeve 39 is positioned in the proximal direction relative to the coupling structure 34 and the counter-coupling structure 40 and releases the latter so that the plunger 15 can be released from the coupling rod 38 while the coupling hooks 36 are rebounding. Now the user may remove the pump module 2 from the mount 30 of the infusion pump 1.

In an emergency case or if the infusion pump 1 has a technical defect, the plunger 15 can be unlocked via an emergency release with the aid of the actuating element 16. Accordingly (cf. FIGS. 4 and 5), the actuating element 16 is manually pushed in the proximal direction (cf. also the arrow on the actuating element 16 in FIG. 1). A driving cam 64 which is in mesh with the control cam 61 of the clamping sleeve 39 slides said control cam with the clamping sleeve 39 to the rear (in the proximal direction) so that the coupling structure 34 and the counter-coupling structure 40 are released and the plunger 15 can be disconnected from the coupling rod 38. For preventing the emergency release from working in the release or pumping position (shown in FIG. 3) and permitting the same to work in the uncoupling or blocking position only (shown in FIG. 2), a web 65 or cam 65 which, when the control link 43 is in the release or pumping position, interacts with the driving cam 64 and prevents a user from inadvertently triggering the emergency release during infusion is provided on the control link 43 (cf. especially FIG. 5). Alternatively, the control link 43 can be controlled via a further linear motor.

The invention claimed is:

1. An infusion system comprising an infusion pump and a pump module being separate therefrom and provided as a disposable product and thus replaceable which is configured to be arranged in a mount of the infusion pump, the pump module comprising a plunger-barrel unit operatively connectable to a drive mechanism of the infusion pump, the pump module further comprising a barrel and a plunger translationally movable within the barrel, the plunger being adapted to be coupled to the drive mechanism by a coupling structure operatively connected to the plunger and by a counter-coupling structure configured for connecting engagement in the coupling structure and being operatively connected to the drive mechanism, wherein the infusion pump has a control link which is operatively connected or operatively connectable to the pump module so that, when the pump module is arranged in the mount, the control link is positioned by force in a release position in which pumping action of the plunger is enabled, the control link being displaceable from the release position to a blocking position that disengages the counter-coupling structure from the coupling structure and allows decoupling of the plunger of the pump module from the drive mechanism of the infusion pump, and wherein the infusion pump includes a cover member configured to be positioned in a closing position closing the mount for the pump module, wherein the cover member, the mount and the pump module are adapted to each other and designed so that, when the pump module is not arranged in the mount, the cover member cannot be positioned in the closing position closing the mount.

2. The infusion system according to claim 1, wherein the cover member is operatively connected to the control link in such a way that the control link is positioned by force into the release position when the cover member is provided in the closing position and is positioned by force into the blocking position when the cover member is not provided in the closing position.

3. The infusion system according to claim 1, wherein the infusion system includes a toggle lever mechanism which is operatively connected to the pump module and operatively connected to the control link.

4. The infusion system according to claim 1, wherein the control link is biased to the blocking position.

5. The infusion system according to claim 1, wherein the infusion system further comprises a securing member configured for locking the coupling structure and the counter-coupling structure in the coupled state to each other in a securing position.

6. The infusion system according to claim 5, wherein the coupling structure comprises a hook, and the counter-coupling structure comprises a groove, wherein the hook is configured for engagement in the groove to couple the drive mechanism to the plunger.

7. The infusion system according to claim 6, wherein the securing member is axially movable relative to the plunger-barrel unit and over the hook when the pump module is arranged in the mount, the securing member being axially movable to a clamping position to lock the hook in the groove to couple the drive mechanism to the plunger.

8. The infusion system according to claim 7, wherein the securing member comprises a clamping sleeve configured to engage the hook and prevent the hook from moving radially outwardly and disengaging the groove.

9. The infusion system according to claim 5, wherein the securing member is operatively connected to the control link in such a way that the securing member fixes the coupling structure and the counter-coupling structure when the control link is provided in the release position, and the securing member releases the coupling structure and the counter-coupling structure when the control link is provided in the blocking position.

10. The infusion system according to claim 5, wherein the securing member is a sleeve-shaped hollow body comprising a longitudinal axis oriented in parallel to an axis of the plunger, and the securing member is positionable relative to the coupling structure and the counter-coupling structure in a direction of the axis of the plunger between the securing position and a release position.

11. The infusion system according to claim 5, wherein the securing member is biased to the securing position.

12. The infusion system according to claim 5, wherein the infusion system includes an emergency release comprising an actuating element coupled to the securing member so as to manually actuate the securing member and to move the securing member from the securing position to a securing member release position.

13. The infusion system according to claim 12, wherein the actuating element is coupled to the control link so that, when the control link is provided in the release position, the control link will block and cannot be actuated for moving the securing member from the securing position to the securing member release position.

* * * * *